United States Patent [19]
Knoblauch

[11] Patent Number: 6,063,629
[45] Date of Patent: May 16, 2000

[54] MICROINJECTION PROCESS FOR INTRODUCING AN INJECTION SUBSTANCE PARTICULARLY FOREIGN, GENETIC MATERIAL, INTO PROCARYOTIC AND EUCARYOTIC CELLS, AS WELL AS CELL COMPARTMENTS OF THE LATTER (PLASTIDS, CELL NUCLEI), AS WELL AS NANOPIPETTE FOR THE SAME

[75] Inventor: Michael Knoblauch, Butzbach, Germany

[73] Assignee: Wolfgang Lummel, Zug, Switzerland

[21] Appl. No.: 09/325,450

[22] Filed: Jun. 3, 1999

[30] Foreign Application Priority Data

Jun. 5, 1998 [EP] European Pat. Off. .............. 98110294

[51] Int. Cl.[7] .................................................. C12N 15/64
[52] U.S. Cl. ......................................... 435/455; 435/285.1
[58] Field of Search ................................... 435/455, 285.1

[56] References Cited

U.S. PATENT DOCUMENTS

| | | | |
|---|---|---|---|
| 3,720,354 | 3/1973 | Drummond et al. | 222/386 |
| 4,625,677 | 12/1986 | Neher | 118/713 |
| 5,225,750 | 7/1993 | Higuchi et al. | 318/280 |

FOREIGN PATENT DOCUMENTS

| | | |
|---|---|---|
| 0 292 899 A2 | 11/1988 | European Pat. Off. . |
| 44 23 267 A1 | 1/1996 | Germany . |
| 196 29 143 A1 | 1/1998 | Germany . |
| 298 01 523 U | 6/1998 | Germany . |
| 2 211 111 | 6/1989 | United Kingdom . |

OTHER PUBLICATIONS

Patent Abstracts of Japan, Higuchi Ryuichi, "Dispensing Apparatus" 05133851, May 28, 1993.

*Primary Examiner*—James Ketter
*Attorney, Agent, or Firm*—Roberts & Mercanti, L.L.P.

[57] ABSTRACT

The invention relates to a microinjection process for introducing an injection substance, particularly genetic material, into procaryotic and eucaryotic cells, as well as cell compartments of the latter (plastids, cell nuclei). It is disadvantageous in the prior art that the cell is damaged by the glass pipette. This problem is obviated by the invention in that the nanopipette (10), which has an external diameter of 0.05 to 0.2 $\mu$m, an internal diameter of 0.1 to 1.5 mm and a tip diameter of 0.025 to 0.3 $\mu$m is used and is filled with the injection substance (1) and a heat-expandable substance or substance mixture and the capillary of the nano-pipette (10) is then sealed with an adhesive, the pipette tip, with the aid of a microscope and a micromanipulator, is stuck into the desired plastids, bacterium or cell compartment/cell nucleus and the nanopipette is heated by means of a regulatable heater (12) until the injection substance passes out of the pipette tip at an outflow rate of up to 1 femtoliter per second and enters the plastids, bacterium or cell compartment/cell nucleus, whose diameter is 1 to 20 $\mu$m.

The invention also relates to the correspondingly filled nanopipette, which is heatable by a regulatable heater for temperature-controlled injection purposes.

9 Claims, 4 Drawing Sheets

(2 of 4 Drawing Sheet(s) Filed in Color)

MICROINJECTION PROCESS FOR INTRODUCING AN INJECTION SUBSTANCE PARTICULARLY FOREIGN, GENETIC MATERIAL, INTO PROCARYOTIC AND EUCARYOTIC CELLS, AS WELL AS CELL COMPARTMENTS OF THE LATTER (PLASTIDS, CELL NUCLEI), AS WELL AS NANOPIPETTE FOR THE SAME

BACKGROUND OF THE INVENTION

The present invention relates to a microinjection process for introducing an injection substance, particularly foreign, genetic material, into procaryotic and eucaryotic cells, as well as cell compartments of the latter (plastids, cell nuclei), as well as to a nanopipette for performing this process.

Intracellular microinjection of fluorescent dyes (Kempers & van Bel 1997), antibodies (Kamei et al, 1996; Oka et al, 1990; Honer et al, 1988), other proteins (Rose et al, 1992; Staiger et al, 1994; Walton et al, 1992) and genetic material (Kost et al, 1995; Nguyen et al, 1996; Heinzel et al, 1997) is a frequently used method, despite several disadvantages associated with sticking or piercing a microelectrode into a cell. The clear disadvantages of the prior art are associated with damage (cytoplasm loss) to the cell through the glass pipette.

To ensure that the cell is not destroyed in an irreparable manner, the plasma membrane surrounding the cell must close round the stuck in tip of the pipette, so as to prevent cell content leakage. This problem frequently arises on sticking micropipettes (tip diameter 0.5 to 1 $\mu$m) into small cells (diameter 10 to 20 $\mu$m). In addition, many cells have a high internal pressure, i.e. the turgor pressure (all plant cells up to 4 MPa [40 bar], procaryotic cells and some animal cells), which clearly worsens the problems. Following piercing there is a pressure discharge round the pipette and via the pipette tip into the pipette interior. The latter phenomenon is made visible by the so-called backfiring of the electrode content (Van der Schoot, 1989). Drastic ultrastructural changes by the piercing of pipettes (tip diameter 1 $\mu$m and greater) could e.g. be revealed in the case of sieve elements (plant tissue) (Knoblauch and Van Bel, 1998). In the case of pipettes with a tip diameter of 0.1 $\mu$m, this phenomenon was not observed. Therefore the aim is to make the pipette tip as small as possible, so that the inflow rate of the cell content into the pipette is lower than the water absorptivity of the cell via its own membrane. Thus, the cell can maintain its internal pressure by water absorption, so as to prevent the backfiring phenomenon. In addition, such a pipette (tip diameter approx. 0.1 $\mu$m, i.e. 25 to 100 times smaller than in the conventional case) would cause a much smaller hole in the plasma membrane of the cell and therefore the leakage problems around the perforation point would be minimized. A good sealing action is also to be expected with very small cells.

DE-C2-37 38 874 uses a microneedle with a tip diameter of approx. 1 $\mu$m, in order to perform a process for producing genetically transformed plant objects by introducing a transforming factor into the recipient or receptor object, namely into a plant protoplast and subsequent selection of cell lines and plants from said object, which have new, hereditary characteristics, macromolecules being used as the transforming factor and the latter is introduced into the recipient object by microinjection, which is characterized in that the transforming factor is either a DNA molecule or an autonomously replicating organelle and the recipient object is either a single cell or one cell in the cell union.

The negative consequence of such a small tip is the very high pressure required for permitting the injection of substances into a cell through the minute opening. Conventional pressure injection equipment is unsuitable for this, because it is not possible to build up the necessary pressure therewith, so as to be able to press sufficient material into the cell in an appropriate injection time (max a few minutes).

SUMMARY OF THE INVENTION

The problem of the invention is therefore to improve the aforementioned process or nanopipette in such a way that it prevents the disadvantages described and permits an easy, rapid and non-destructive introduction of injection substance into procaryotic and eucaryotic cells, as well as cell compartments of the latter.

It has therefore been found that piercing is possible in not previously reachable compartments or procaryotic cells, without there being a cytoplasm loss thereof.

The nanopipette according to the invention is based on the fact that the heat-induced expansion of a substance or substance mixture with which the pipette is filled, forces the substance to be injected out of the pipette tip, which has a diameter of only 0.025 to 0.3 $\mu$m, particularly 0.05 to 0.2 $\mu$m and, as a function of the filling substance or substance mixture, it is possible to build up the desired pressures in stepwise manner.

DETAILED DESCRIPTION OF THE PREFERRED EMBODIMENT

Figure 1:
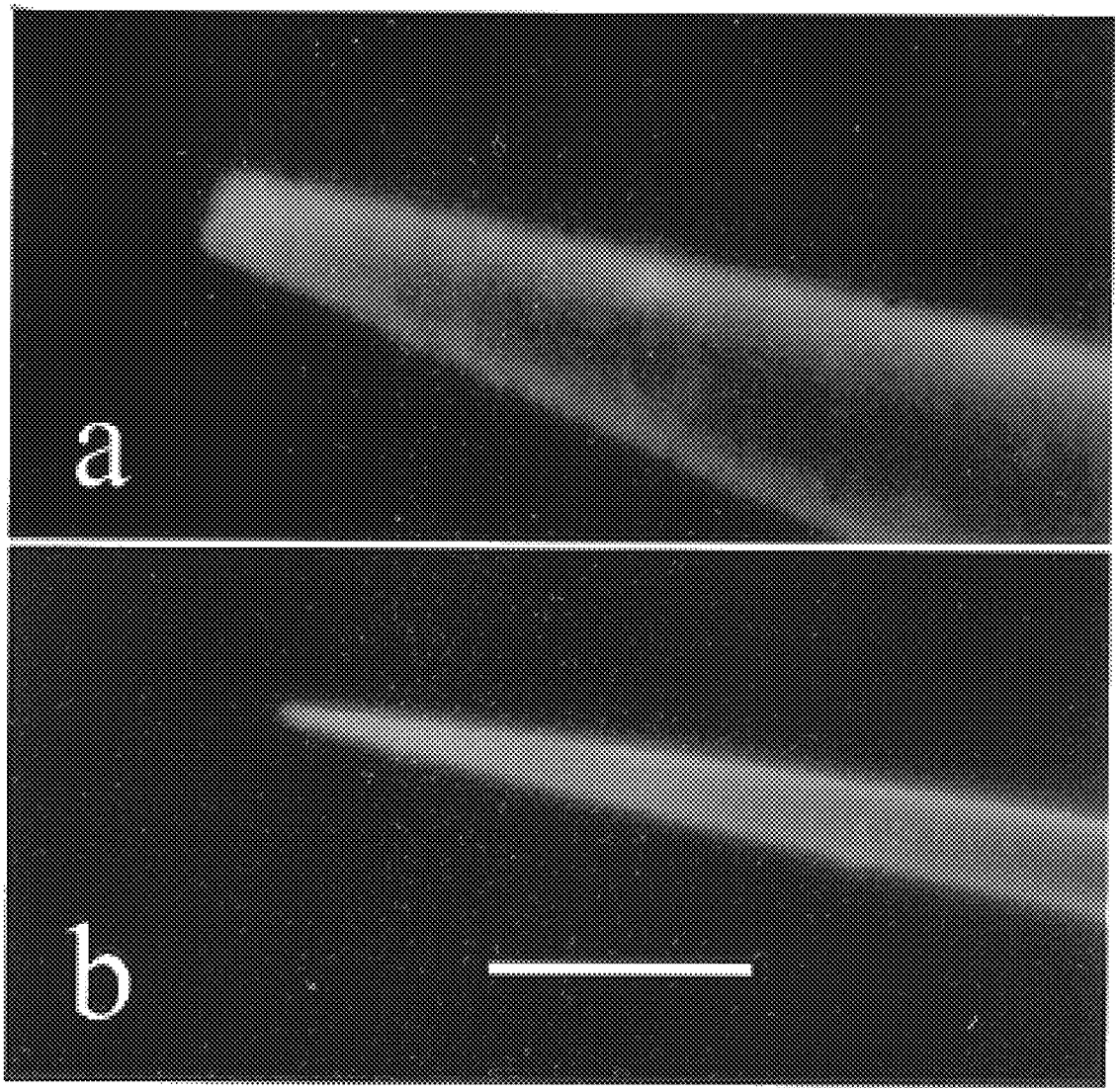

Fundamentally the most varied liquids or solids can serve as the filling substance or substance mixture. What is decisive for the usability of such a substance or mixture is its expansion coefficient compared with the expansion of the glass walls of the nanopipette, because the latter also expand on heating. Tests have revealed that expansion coefficients in the range of those of metals are the most ideal. However, for filling purposes, in the metal sector it is only possible to use low-melting alloys or pure metals (max up to +200° C.), because the filling substance must be filled in the liquid state. At higher temperatures the glass walls of the pipette would become soft and the small tip would melt. Therefore mercury would be an ideal candidate, because it is already liquid at ambient temperature. However, it suffers from the unavoidable disadvantage that it is highly toxic for living cells and is consequently unusable. In addition, it cannot be used in open systems. Other low-melting alloys with a melting point between +50 and +200° C. (e.g. lead-tin eutectic) can be filled into the pipette after melting. The metal is detached from the glass wall on cooling. The minor gap which occurs between the metal and the glass wall and extends into the tip can subsequently be filled with the substance to be injected. Following pressure-tight sealing of the back and slow heating again, the metal again starts to expand and presses the injection substance through the tip. The disadvantage of this procedure is that on cooling the metal generally becomes detached from the wall in an irregular manner and small crystals are formed. Thus, a bubble-free filling of the electrode is scarcely possible. Thus, due to the high compressibility of the remaining gas bubbles, the pressure rises much more slowly. However, it is pointed out that such a system is serviceable within the scope of the invention.

The above-described problems do not arise with substances which are liquid at room temperature. The pipette can be filled at room temperature and no irregularities occur in the surface and there are also no crystallization phenomena. Thus, such substances are fundamentally preferred. As stated hereinbefore, mercury is the only pure metal which is liquid at room temperature, but is unusable as a result of its toxicity. Other organic liquids such as silicone oil, etc. have excessive expansion coefficients. In tests performed with pure silicone oil breathing or emission of body heat by the person carrying out the test in front of the microscope was sufficient to cause a massive outflow from the pipette tip. Such a system is much too temperature-sensitive to permit a rational control thereof.

However, the ideal, preferred filling material proved to be a newly developed gallium-indium-tin alloy (Galinstan, trademark of Geraberger Thermometerwerke, Geschwenda, DE [cf. EP-B1-657 023]). This metal alloy is liquid up to 20° C. According to present scientific knowledge it is completely non-toxic and at $11.5\gamma\ 10^{-5}K^{-1}$ has a volume expansion coefficient of approximately 63% compared with that of mercury ($18.1\gamma\ 10^{-5}K^{-1}$). The low expansion coefficient means that when Galinstan is used alone the pressure is built up very slowly. However, what is important for biological samples is that there is no rise above or drop below certain temperature ranges. An excessive sensitivity, like that of silicone oil, leads to the pipette not being correspondingly controllable. However, an inadequate sensitivity means that the pipette must be excessively heated for biological samples in order to build up the necessary pressure and the samples could be damaged. Thus, preference is given to a combination of Galinstan and silicone oil. This two-component filling material mixture combines the strong expansion of silicone oil with the weak expansion of Galinstan. Thus, the more silicone oil that is used compared with Galinstan, the more heat-sensitive the pipette. This makes the pipette very variable and it can be adapted in optimum manner to all conditions for the most varied injections, which take place in the case of biological samples in the temperature change range of 5 to 10° C. The Galinstan to silicon oil quantity ratio with a borosilicate glass nanopipette is 4:1.

Fundamentally, all glass types can be used for producing the glass pipettes, which are normally used for the production of pipettes or microelectrodes (e.g. borosilicate glass, quartz glass). However, it is advantageous for certain applications if specific glass types are used. For example, for piercing in small cell compartments (chloroplasts, etc.) and the subsequent heating of the pipette by expansion of the glass there is a migration through the compartment. It is advantageous in such cases to use quartz glass, because it has a 10 to 20 times lower expansion coefficient than other glass types.

The pipette is filled in the following way. Capillaries with an inner filament are used. After drawing out the capillary to the pipette, the tip is firstly filled with the substance to be injected by means of the capillary forces acting on the filament. Then Galinstan and silicone oil follow in the corresponding quantities. When the pipette is completely filled in bubble-free manner, its end is sealed in pressure-tight form. Sealing advantageously takes place with the aid of an approximately 1 cm long glass cap, whose internal diameter is slightly larger than the external diameter of the pipette. The glass cap is filled with a two-component adhesive and inverted over the back of the pipette. Following the hardening of the adhesive, the pipette is sealed in pressure-tight manner by the small gap between cap and pipette and the shear forces acting on the adhesive in the longitudinal direction. When working with extremely high pressures, the back of the pipette can also be drawn out to a tip. As the pressure acts per surface area, the decrease in the surface area leads to a reduction of the pressure acting on the cap. Thus, a pressure-tight seal is ensured even under maximum pressures. The adhesive should be a two-component or polymerization adhesive, because on heating they are only subject to limited shrinkage. Adhesives with solvents have a much greater shrinkage, because the solvent volatilizes.

There are various possibilities for a heater. It is important that the heater is not connected to the pipette, so as to prevent vibrations. Advantageously, an air flow provided by a pump is blown by means of a hose and a glass capillary onto the pipette (FIG. 3), the air flow being directed away from the product. Around the glass capillary is wound a constant wire (heating wire), which is connected to a continuously variable power supply. Heating of the heating wire leads to the air flow being heated and ultimately the pipette. As the pipette is filled with metal, induction heating systems and the like could also be used.

Numerous advantageous result from the pipette according to the invention and include the possibility of injecting in procaryotic cells (bacteria, etc., FIG. 4a), plastids such as chloroplasts (FIG. 4b), cell nuclei (FIG. 5a, b), etc. Cell nucleus injections are routinely performed in the case of animal cells by pipettes with tip diameters of 0.5 to 1 μm. However, the novel, temperature-controlled nanopipette has a 25 to 100 times smaller tip area than the conventional pipettes, so that greatly reduced damage is to be expected. For the first time it is possible to reach cell nuclei or cell compartments in highly turgescent plant and animal cells (FIG. 4b) without causing a pressure loss in the cell. Thus, for the first time, microinjection possibilities are available to the microbiologist. The injection of macromolecules, which are essential in certain spheres of genetics, as well as for cellular and medical research, can be performed with reduced cell damage and through the injection of smaller quantities. In general, more precise working is possible. The preheating of the pipette and cooling after piercing offer the possibility of extracting cellular fluids or juices from compartments.

Numerous pipette design variants exist. It can be adapted to experimental requirements by (a) modifying the internal diameter of the glass capillary, (b) modifying the ratio of the filling materials, (c) adapting the tip diameter, (d) using different glass types, etc.

The file of this patent contains at least one drawing executed in color. Copies of this patent with color drawing (s) will be provided by the Patent and Trademark Office upon request and payment of the necessary fee.

Preferred embodiments of the invention are described in greater detail hereinafter relative to the drawings, wherein show:

FIG. 1a A scanning electron micrograph of the front part of a conventional pipette (tip diameter approx. 0.7 μm).

FIG. 1b A temperature-controlled nanopipette according to the invention (tip diameter approx. 0.1 μm).

Figure 2:
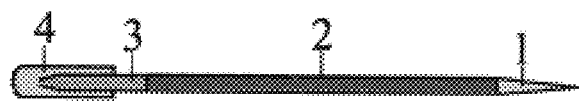

FIG. 2 A diagrammatic representation of an inventive, completely filled, temperature-controlled nanopipette (10), after filling it with injection substance (1), Galinstan (2) and silicone oil (3) the capillary is sealed with an adhesive-filled glass cap (4).

Figure 3:
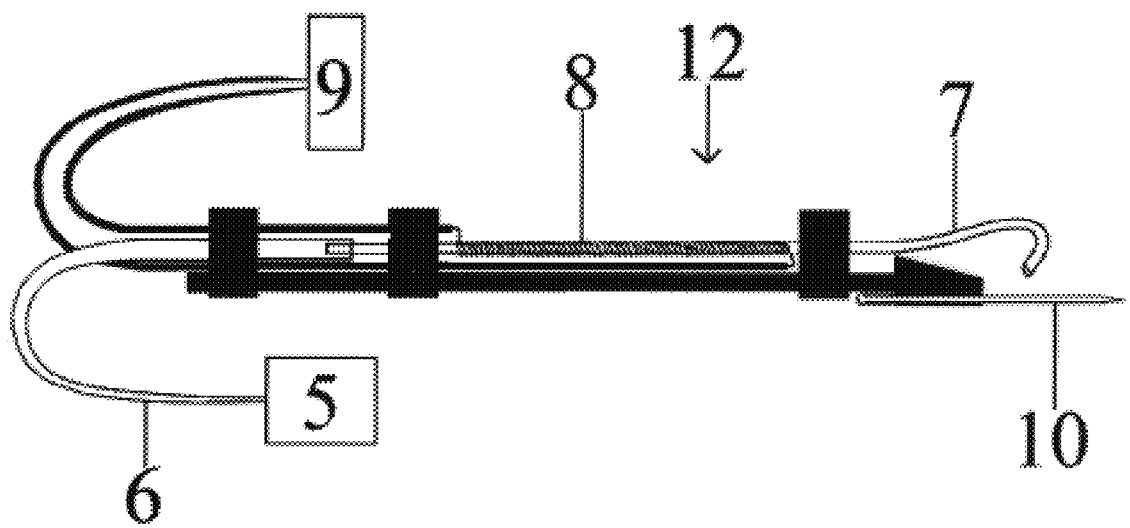

FIG. 3 A diagrammatic representation of the inventive heater, an air flow produced by a pump (5) being blown via a hose (6) and glass capillary (7) onto the pipette (10), the air being heated by a constantan wire (8) wound round the glass capillary (7) and connected to a continuously variable power supply.

Figure 4:
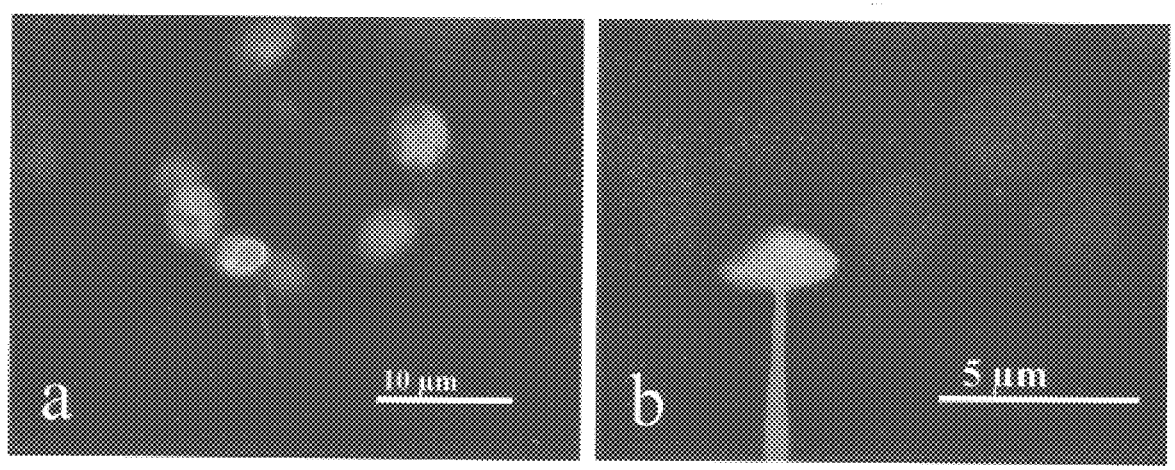

FIGS. 4a and 4b Confocal laser scanning micrographs of microinjections using the temperature-controlled nanopipette according to the invention: (a) injection of Lucifer Yellow (green=brightest point in the s/w image) into a single cell of the cyanobacterium Nostoc muscorum (procaryot); red (=gry points) auto-fluorescence of chlorophyll; (b) injection of Lucifer yellow (green) into a single chloroplast of a Vicia faba mesophyll cell; the other chloroplasts being detectable as red-fluorescing substances.

Figure 5:
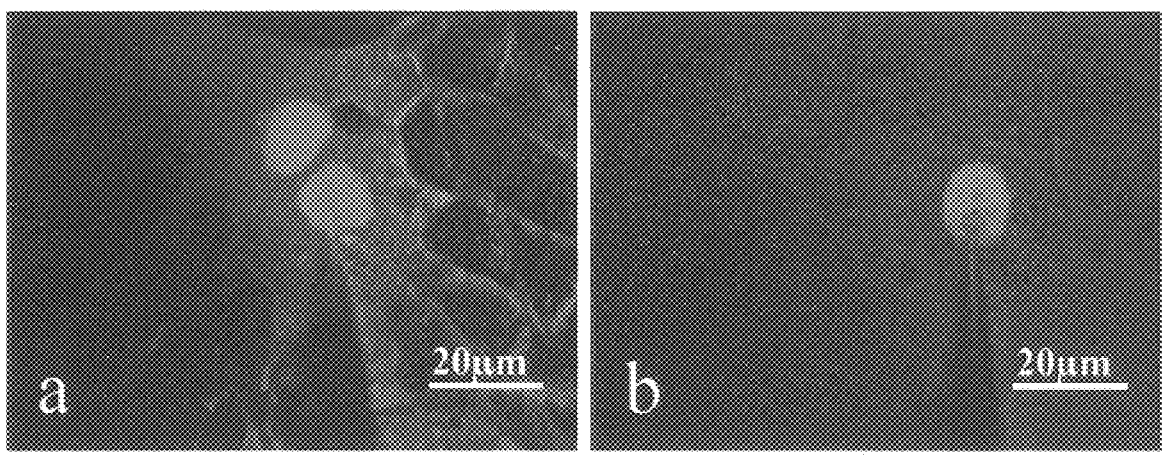

FIGS. 5a and 5b Confocal laser scanning micrographs of microinjections with the inventive temperature-controlled nanopipette in the nuclei of cells of xenopus distal renal tube A6 cell line cultures: (a) Lucifer Yellow (approx. 0.5 kDa) injected into the lower nucleus and rapidly leaving the latter via the nuclei pores and also accumulated in the other nucleus; (b) whereas a 70 kDa dextran Lucifer Yellow conjugate only leaves the nucleus very slowly.

What is claimed is:

1. A microinjection process for introducing an injection substance into procaryotic or eucaryotic cells, or cell components of the latter by means of a nanopipette and pressure, comprising filling a nanopipette, which has an external diameter of 0.5 to 2 mm, an internal diameter of 0.1 to 1.5 mm and a tip diameter of 0.025 to 0.3 $\mu$m, with an injection substance and a heat-expandable substance or substance mixture, sealing a capillary of the nanopipette with an adhesive, sticking the nanopipette tip with the aid of a microscope and a micromanipulator into the cell or cell compartment, and heating the nanopipette by means of an adjustable heater until the injection substance passes out of the nanopipette tip at an outflow rate of up to 1 femtoliter per second and enters the cell or cell compartment.

2. The microinjection process according to claim 1, wherein an air flow produced by a pump is blown by means of a hose and glass capillary onto the nanopipette, the air being heated by means of a constantan wire wound around the glass capillary and connected to a continuously variable power supply.

3. The process according to claim 1 wherein the nanopipette is sealed by means of a two-component adhesive and a glass cap.

4. The process according to claim 1 wherein 0.1 to 100 femtoliters of injection substance are pressed within 5 minutes into the cell or cell compartment.

5. The process according to claim 1 wherein the heat-expandable substance or substance mixture comprises a non-toxic, pure metal or metal alloy with a melting point between $-20$ and $+200°$ C., which has an expansion coefficient of about that of mercury.

6. The process according to claim 5, wherein the non-toxic metal alloy comprises a gallium-indium-tin alloy which is liquid down to $-20°$ C. and has a volume expansion coefficient of $11.5\gamma \ 10^{-5}K^{-1}$.

7. The process according to claim 6, wherein the substance mixture comprises a silicone oil.

8. The process according to claim 7, wherein the substance mixture comprises four parts of a metal alloy and one part of a silicon oil.

9. An apparatus comprising a nanopipette having an external diameter of 0.5 to 2 mm, an internal diameter of 0.1 to 1.5 mm and a tip diameter of 0.025 to 0.3 $\mu$m, and an adjustable heater connected to the nanopipette.

\* \* \* \* \*